(12) United States Patent
Cappola

(10) Patent No.: US 6,562,871 B1
(45) Date of Patent: May 13, 2003

(54) DRY GRANULATION OF PHARMACEUTICAL FORMULATION COMPRISING MEXILETINE

(75) Inventor: Michael L. Cappola, Wilton, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 10/041,834

(22) Filed: Oct. 25, 2001

Related U.S. Application Data

(63) Continuation of application No. 09/706,627, filed on Nov. 6, 2000.

(51) Int. Cl.[7] ............ A61J 3/02; A61K 31/138
(52) U.S. Cl. ............... 514/651; 564/443
(58) Field of Search ............ 564/443; 514/651

(56) References Cited

U.S. PATENT DOCUMENTS

| | | | | |
|---|---|---|---|---|
| 3,659,019 A | * | 4/1972 | Koppe et al. | 424/330 |
| 4,031,244 A | * | 6/1977 | Koppe et al. | 424/330 |
| 6,056,968 A | * | 5/2000 | Gilbert et al. | 424/422 |

* cited by examiner

*Primary Examiner*—Mukund J. Shah
*Assistant Examiner*—Thomas C McKenzie
(74) *Attorney, Agent, or Firm*—Robert P. Raymond; Mary-Ellen M. Devlin; Alan R. Stempel

(57) ABSTRACT

Compaction of mexiletine hydrochloride crystals is described, which provides a powder suitable for use in capsules without use of organic solvents.

2 Claims, 3 Drawing Sheets

DRY GRANULATION OF PHARMACEUTICAL FORMULATION COMPRISING MEXILETINE

This application is a continuation of U.S. Ser. No. 09/706,627 filed Nov. 6, 2000.

BACKGROUND OF THE INVENTION

Mexiletine, 1-(2,6- dimethyl-phenoxy)-2-propanamine, is an approved and well-known pharmaceutical useful as an anti-arrhythmic. Its structure and use are described in U.S. Pat. Nos. 3,659,019 and 3,954,872. Pharmaceutical formulations comprising mexiletine are described in U.S. Pat. No. 4,031,244.

Mexiletine hydrochloride is a finely divided, crystalline substance and is used in commercial pharmaceutical formulations for mexiletine. However, the hydrochloride has a low bulk density, and so consequently also provides a large bulk volume. One commercial mexiletine product, sold under the trademark MEXITIL by Boehringer Ingelheim Pharmaceuticals, Inc., is a capsule where the hydrochloride represents approximately 62% (w/w) of the fill weight of the capsule. The inert excipients in the MEXITIL product include corn starch (bulking agent and granulation aid), colloidal silicon dioxide (drying agent and to prevent granulation caking), and magnesium stearate (lubricant). During processing to manufacture the MEXITIL product, a 1:1 solution of purified water and SD3A (specifically denatured ethanol for pharmaceutical use) alcohol is prepared. This solution is then used to increase the density of the above-mentioned MEXITIL ingredients (except magnesium stearate). The wetted combination is then dried (to evaporate or remove the water/denatured ethanol), sized by milling and then combined with the lubricant magnesium stearate. This final blend is then filled into capsules.

As indicated above, a solution of water and denatured ethanol is prepared in order to increase the density of the mexiletine hydrochloride blend. This is necessary in order to produce a powder that can be effectively handled and placed into capsules. Use of water alone does not achieve the necessary and required densification of the powder blend. However, current and future environmental regulations restrict the amount of organic solvent emissions into the atmosphere. Accordingly, the current manufacturing process for the MEXITIL product will become more costly and less efficient as such emissions become more restricted.

BRIEF SUMMARY OF THE INVENTION

A dry, granulation process involving roller compaction results in a powder blend of mexiletine hydrochloride suitable for use in capsules. Dry granulation and compaction does not result in emission of organic solvents into the atmosphere.

DETAILED DESCRIPTION OF THE INVENTION

Figure 1:
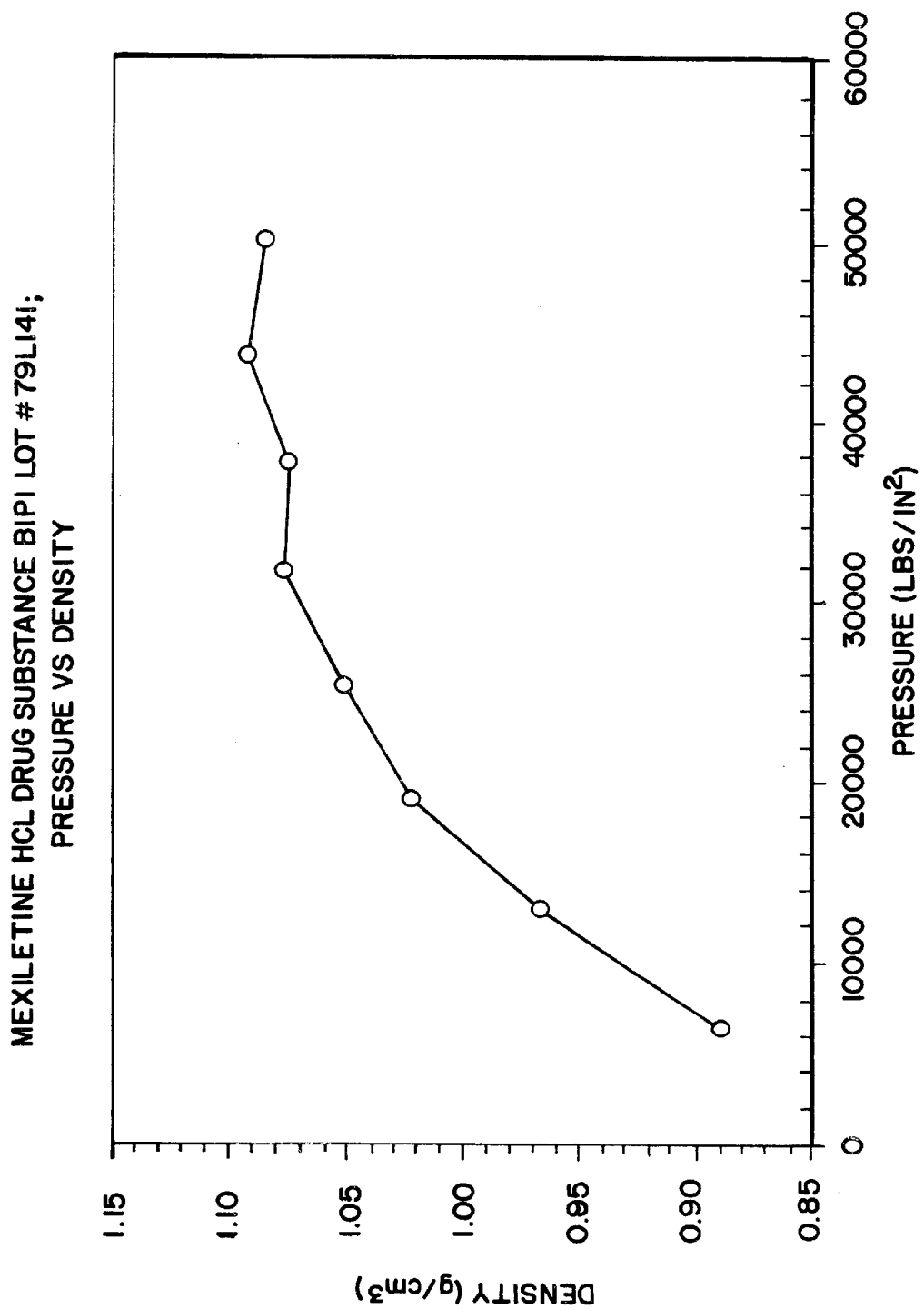
FIG. 1 is a graph showing density of mexiletine hydrochloride at various pressures.

Described below is a process for compaction of a pharmaceutical formulation comprising mexiletine. For purposes of completeness, the equipment and methods used to both produce and test the "dry" formulation are described. The "wet" formulation comprising mexiletine was obtained from the commercial MEXITIL product, sold by Boehringer Ingelheim Pharmaceuticals, Inc. as noted above.

For purposes of understanding the invention described hereinbelow, the following equipment was used:

Bright-Line Hemacytometer; Reichert Scientific Instruments, Buffalo, N.Y.

Carver Laboratory Press, Model C; Fred S. Carver Inc., Menomonee Falls, Wis.

Erweka Oscillating Mill, AR400 Drive, FGS Granulator, Erweka Instruments, Milford, Conn.

Fitzpatrick Roller Compactor, Model IR 520; The Fitzpatrick Co., S. Plainfield, N.J.

Flow Apparatus: Funnel (top 150 mm, length 135 mm, bottom 24 mm) Agitator Vibro Graver Model 74; Burgess Business Products, New York Mills, N.Y.

Hewlett Packard HP 1046A Programmable Fluorescence Detector, Hewlett Packard Company, Paramus, N.J.

Hofliger and Karg Capsule Machine, GKF 330, Robert Bosch, GMBH, Germany.

Olympus BY2 Polarizing Microscope, Olympus Optical Co. Ltd, Japan.

Olympus SZH Stereo Microscope, Olympus Optical Co. Ltd, Japan.

Starrett Thickness Gauge, Model 1010 M2; The Starrett Co., Athol, Mass.

Turbula Mixer, Type 12C; Glen Mills Inc., Maywood, N.J.

Van Kel Dual Density Tapper, Model 50-1200; Van Kel North America, Edison, N.J.

Van Kel VK 7000 Dissolution Testing Station, VK 8000 Dissolution Sampling Station, Van Kel North America, Edison, N.J.

Water Model 510 Solvent Delivery Pump, Wqters 680 Automated Gradient.

Controller, Waters 717 Plus Autosampler, Waters Corp., Milford, Mass.

Also, the following materials were used in the examples set forth below:

Colloidal Silicon Dioxide NF.

Corn Starch NF.

Empty gelatin capsules, size #1, Shionogi, cap EKO opaque red # 181, body EKO, opaque red #181.

Magnesium Stearate NF.

Mexiletine HCI Drug Substance.

Mexiletine "Wet" Granulation Material taken from MEXITIL® capsules.

Also, the following techniques were used in evaluating materials made according to the present invention and prior art mexiletine.

Sieve Analysis

Sieve analysis was performed using an ATM sonic sifter and 5 g of the drug substance mixed with 100 mg colloidal silicon dioxide (CSD). The CSD was necessary to prevent self association by the mexiletine particles. The two were mixed gently by hand stirring with a spatula in a beaker. The equipment was set to run for 2 minutes with sift and pulse at amplitude #6. Sieves were nested in the following order: #18 mesh (1000 $\mu$m), #35 mesh (500 $\mu$m), #60 mesh (250 $\mu$m), #120 mesh (125 $\mu$m), #230 mesh (63 $\mu$m), and fines pan (<63 $\mu$m). Samples were run in duplicate and the generated percent retained reflect the average of the two measurements.

Pour and Tap Density

Pour and tap density were tested using a Van Kel dual tapper and a 100 mL fluted graduate. The tare weight of the graduate was determined. It was then filled by pouring the powder into the graduate to approximately 70 mL. The net weight was next determined and a pour density calculated by dividing the net weight by the observed volume. Tap density was determined by allowing the graduate to tap 1000 times and reading the new volume. Tap density was calculated by dividing the net weight by the new "tap" volume. Both measurements were expressed in grams/mL. Results were reported as the average of two measurements.

Compressional Force Profiles

Compressional force profiles were generated on a calibrated Carver press using 12 mm standard cup punches and matching die. The punches and die were dusted with magnesium stearate to facilitate the release of the slug from the die. Five hundred milligram aliquots of drug substance were weighed and individually loaded into the die for compression. Slugs were compressed at 1000, 2000, 3000, 4000, 5000, 6000, 7000 and 8000 pounds gauge force (unless otherwise noted). Gauge force readings were corrected based on the calibration for that gauge and press. The compressed slugs for each representative force were weighed on a four place balance and measured for thickness. Pressure, volume and density were calculated using slug (tablet) geometry and area.

Flow Studies

The flow studies were performed using a ring stand and funnel set-up, such that the funnel was perpendicular to the table flat surface and the tip of the funnel was 6 inches from the table flat surface. The funnel was plastic with the following dimensions: upper diameter, 150 mm, lower diameter 24 mm, and overall length 135 mm. To the upper, wider diameter of the funnel a vibrator was placed touching the outer perimeter. The vibrator was set on its dial such that the indicator was in the 3 o'clock position. Fifty grams of material was placed into the funnel while holding a piece of cardboard under it. The vibrator was started, and the cardboard was removed while simultaneously starting a timer. The time for the fifty grams to pass through a funnel was recorded. The angle of repose, the maximum angle that can be obtained between the free standing surface of a powder heap and the horizontal plane, was calculated according to:

$$\tan \Phi = 2 \, h/D$$

Where h is the height of the powder heap and D is the diameter of the base of the powder heap. Tests were performed in duplicate.

Microscopy

Particle size and distribution was determined by suspending a sample of powder in mineral oil on a hemacytometer and counting particles in the size ranges: 1–5, 5–10, 10–25, 25–50, 50–100, 100–200, >200 $\mu$m using a polarizing light microscope. At least 200 particles were counted.

Maximum and minimum particle sizes were determined with a large sampling using a low power, stereo microscope. The sample was suspended in a well slide filled with mineral oil. Measurements of the largest and smallest particles were made with a calibrated reticule.

The following formulation (Formula Blend) was prepared.

TABLE 1

Formula Blend

| Ingredient | mg/capsule |
| --- | --- |
| Mexiletine HCl | 200 |
| Corn starch | 108 |
| Colloidal silicon dioxide | 8 |
| Magnesium stearate | 4 |
| Total weight | 320 |

The Formula Blend (Table 1), whether at small scale (~240 g) or larger scale (~10 kg), was prepared in a similar manner. The combined powders were delumped through a wire mesh screen (#18–#20 mesh) and then mixed in a small container or drum at ~30 rpm for 5 minutes.

Testing was performed on Formula Blend and the drug substance (Mexiletine HCl) alone and included sieve analysis, pour and tap density, compressional force profiles and flow studies.

Roller Compaction

A 10 kg batch of Formula Blend was prepared and compacted on a Fitzpatrick roller compactor with 0.05 inch full grooved axial rolls. Process settings are set forth in Table 2.

TABLE 2

Process Settings-Roller Compactor

| Item | Setting |
| --- | --- |
| Hydraulic Pressure Setpoint | 400 lbs/in$^2$ |
| Roll Gap Range | 0.14–0.02 inch |
| Vertical Screw Speed | 350 RPM |
| Horizontal Screw Speed | 80 RPM |

In-process compacted material was sampled by taking samples approximately every 5 minutes. This was accomplished by collecting compacted material for a 10-second duration in a plastic bag.

After the compaction of the batch, there was a significant amount of fines which did not compact due to the small batch size. The entire batch was sieved through an #18 mesh hand screen. The compacts were removed, and fines which passed through the screen were recycled into the compactor a second time. The recycled material was likewise sampled for testing.

In-Process Testing of Compacted Samples

Fines

The entire time segment sample was weighed and then hand sieved through a #18 mesh (1000 $\mu$m) hand screen to separate the compacts from the fines. Weight/weight percentages of the compacts (>#18 mesh) and the fines (<#18 mesh) were determined.

Stick Thickness

Stick thickness was determined for 10 sticks for each time segment sample. This was accomplished by measuring the barrel thickness or the cylinder diameter of the stick using a thickness gauge. The average, standard deviation, and relative standard deviation were determined.

Stick Density

Stick density was determined with 6 sticks for each time segment sample. Into a 100 mL glass graduate approximately 70–75 mL of heavy mineral oil was added. The graduate with the oil was weighed and the weight and volume were recorded. Approximately 6 whole sticks were added to the oil. Again, the new weight and volume were recorded.

The stick density equals the difference in weight of the graduate with sticks minus the weight with oil alone divided by the difference in volume of the graduate with the sticks and that with just the oil. The density was expressed in g/mL.

Milling of Compacted Material

Milling

The compacted material was milled with an oscillating mill through a #18 mesh screen at medium speed. The material was sampled at the end of the process for testing.

Evaluation of Milles Compacted Material

The testing performed on the milled, compacted material included sieve analysis, pour and tap density and flow studies. This testing was similar to the previous testing; however, the sieve analysis did not use colloidal silicon dioxide (CSD) since there was no evidence of particle caking.

Encapsulation of the Compacted and Milled Material

Encapsulation

One hundred empty gelatin capsules were weighed to calculate the average empty capsule weight (empty capsule weight=74.25 mg). To this a net fill Of 320.00 mg (equivalent to 200 mg active drug) was added to generate the theoretical filled capsule weight (theoretical filled capsule weight=394.25 mg). The capsule machine was run at 5 rpm (180 capsules/minute) with #1 capsule tooling. Initially an 18.0 mm dosing disk was tested. However for better weight control, a 15.5 mm dosing disk was selected and used to prepare all test samples.

In-Process Testing

The process was run for approximately 1 hour. Samples of capsules were taken over a one-minute time interval at the start of the run (0 time) and at 15, 30, 45, and 60 minutes. Samples of 20 capsules for each time point were tested for weight variation. Average, standard deviation and relative standard deviation were determined for each time point sample of 20 capsules.

Initial Time Testing

Dissolution and Content Uniformity Testing

Dissolution (n=18 capsules) and content uniformity testing (n=15 capsules) were performed with capsules randomly sampled from the bulk according to the USP/NF monograph for Mexitil® capsules. [The United States Pharmacopeia—USP 23, The National Formulary—NF18 United States Pharmacopeia Convention, Inc., Rockville, Md. (Jan. 1, 1995, p. 1024).].

Encapsulation of Commercial Granulation

Granulation from the commercial manufacture of Mexitil® capsules was supplied by the manufacturer. This material was completely processed but not encapsulated. Encapsulation took place under the same conditions as that for the dry granulation (except for changing the disk thickness for the correct fill weight). The evaluation of the powder blend and testing of the capsules were also performed in the same manner as for the dry granulation.

Results and Discussion

Mexiletine Drug Substance

The mexiletine drug substance had a large bulk volume with a low bulk (0.22 g/mL) and tap density (0.35 g/mL). The powder would not flow through a funnel without a vibrator assistance, and then only at a relatively slow rate of 2.1 g/sec.

TABLE 3

Powder Characteristics of Mexiletine Drug Substance

| | |
|---|---|
| Bulk Density (g/mL) | 0.22 |
| Tap Density (g/mL) | 0.35 |
| Flow Rate (g/sec) | 2.1 |
| Angle of Repose (°) | 62 |

The measured angle of repose was 62° (Table 3). Although sieve analysis was performed, the powder cohesiveness prevented accurate measurement even with the addition of colloidal silicon dioxide as an anti-caking aid. This was verified by light microscopy in which individual powder particles could be viewed. Microscopic particle distribution is described in Table 4.

TABLE 4

Particle Size Distribution of Mexiletine Drug Substance

| Size Range ($\mu$m) | %* |
|---|---|
| 1–5 | 32.0 |
| 5–10 | 23.3 |
| 10–25 | 37.9 |
| 25–50 | 6.6 |
| 50–100 | 0.2 |
| 100–200 | 0.0 |
| >200 | 0.0 |

*By Number

Additional testing using larger sample sizes and the "well slide technique" indicated that there were some larger particles equal to 150 $\mu$m. However, these were very few.

It can be anticipated, therefore, that with a low-bulk density (<0.3 g/mL), a relatively slow assisted powder flow, a large angle of repose (>40°), small particle size and a large degree of powder cohesiveness, the active ingredient (comprising 62% by weight of the active fill weight) would have a significant negative impact on overall blend flow and uniformity.

In fact, this is the reason why the current commercial product is wet granulated. This process increases overall powder density, flow, and decreases powder cohesiveness. The wet granulation process is performed with a 1:1 ratio of SD3A alcohol and purified water added to the formula mix (excluding the lubricant). However, as shown herein, mexiletine drug substance and the formula mix can be dry granulated by compaction under pressure to produce a final product with the same characteristics.

Since drug load in the final blend is high, an evaluation of the compressibility of the drug substance alone was first done. Slugs of the pure active ingredient were prepared at different compressional forces on a manual hydraulic press.

FIG. 1 shows that the drug substance has very good compressional characteristics. There was a steady increase in powder density from approximately 6,600 psi to 32,000 psi. Increases in pressure beyond 40,000 psi resulted in some variability in density. Maximum increases in density with pressure occurred between 6,600 and 25,000 psi., indicating that even at lower pressures the drug substance could be compacted with a significant increase in density. Based on these data, it was therefore concluded that mexiletine drug substance was a suitable candidate in itself for densification by compaction.

Formula Blend

The Formula Blend ingredients are presented in Table 5.

TABLE 5

Formula Blend

| Ingredient | Net Fill (mg/capsule) | % w/w |
|---|---|---|
| Mexiletine HCI | 200.00 | 62.50 |
| corn starch | 108.00 | 33.75 |
| colloidal silicon dioxide | 8.00 | 2.50 |
| magnesium stearate | 4.00 | 1.25 |
| total capsule net weight | 320.00 | |

The corn starch acts as a granulating aid and bulking agent; the colloidal silicon dioxide (CSD) aids in the flow and minimizes caking during granulation/milling and the magnesium stearate is the lubricant. Generally it is recommended that the CSD be used in concentrations which do not exceed 0.3% w/w of the formula weight. CSD has a very low bulk density (<0.1 g/mL) and although it is a very effective flow aid, high concentrations may have negative effects on obtaining satisfactory blend density. The current commercial formula is first mixed (all ingredients except lubricant), then wet granulated, dried, milled and mixed with lubricant and finally encapsulated.

Evaluation of the "dry-mixed" formula blend (all the dry ingredients) indicated that, like the mexiletine active ingredient alone, the mix had a low bulk and tap density. The bulk and tap densities, respectively, were 0.23 g/mL and 0.43 g/mL. The powder would not always flow through the funnel without vibrator assistance, however, due to the large amount of CSD. Once powder movement started, it usually progressed very rapidly with average flow rates of 4.3 g/second and an angle of repose of 11° (Table 6).

TABLE 6

Powder Characteristics of Formula Blend

| | |
|---|---|
| Bulk Density (g/mL) | 0.23 |
| Tap Density (g/mL) | 0.43 |
| Flow Rate (g/sec) | 4.3 |
| Angle of Repose (°) | 11 |

Figure 2:
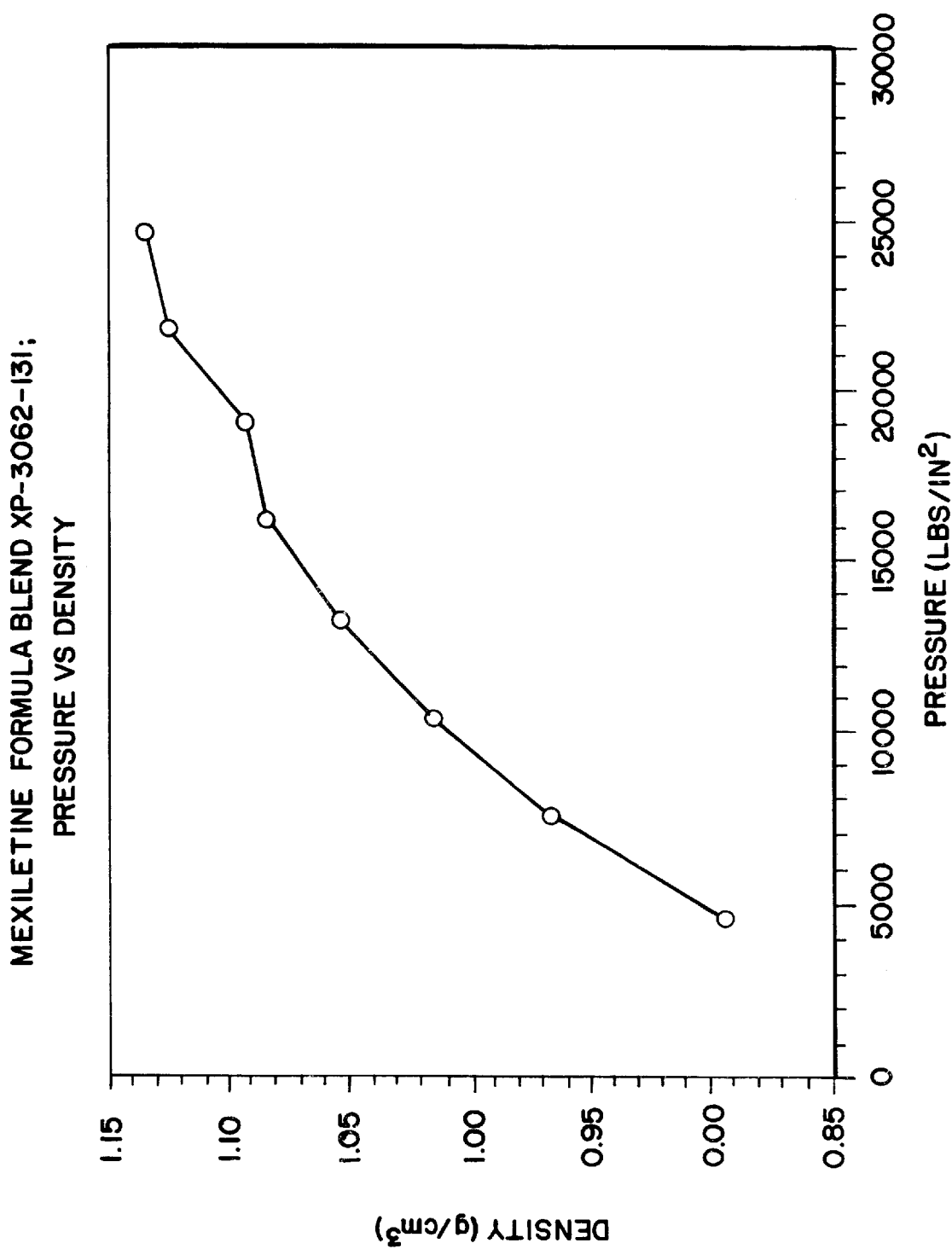
FIG. 2 is a graph showing density of a mexiletine hydrochloride formula blend.

The compressional force profiles performed on the "dry mixed" formula blend and compared to the drug substance alone indicated that both were very compressible with the formula blend showing a slightly better compressibility evidenced by greater density at corresponding pressures (FIG. 1 and FIG. 2).

Roller Compacted Formula Blend

Since the evaluations of the drug substance and formula blend indicated that both materials were compressible over a large range of compressional force, the formula blend was tested on a commercial roller compactor. The compaction pressure was set at the minimum compaction pressure which would produce sticks that would not crumble under gentle, hand-applied pressure. This translated to an applied pressure of approximately 20,000 psi. in the roller compactor. Minimal compaction pressure is preferred to accomplish dry granulation since the powder will be compressed again into tablets or capsule slugs and recompression will only be possible if the starting material hasn't been "overcompressed". Too much compressional force may also lead to decreases in dissolution, degradation of active ingredient and/or energy waste.

A 10 kg batch of formula blend was prepared and compacted into sticks by using grooved axial rolls. In-process samples were taken to determine stick thickness, stick density, and percent fines. The uniformity of stick thickness and density are good indicators of the metering of material into the rolls for compression and the uniformity of that compression. Based on experience, compacts with more than 20% w/w fines (particles smaller than #18 mesh) in a blend intended for recompression into tablets or capsules, will produce poor flow. Therefore the weight of fine particles generally should be below 20% w/w, and ideally below 10% w/w.

Stick thickness was very uniform over time as can be seen from the Table 7. Although the stick thickness varied from 3.84 mm to 4.32 mm, the individual time samples were extremely tight with a coefficient of variation of no greater than 1.56%. Differences between time samples were due to small control changes made on the equipment by the operator. The fines during the process varied from 9.2% to 11.3% except at the end of the run when a substantial amount of uncompacted material did fall between the rolls. The stick density of the time samples had an average of 0.94 g/mL with a range of 0.81 to 1.0 g/mL. These results indicated that overall the process was very uniform and that from a physical processing standpoint, the material was suitable for the dry granulation process by roller compaction.

TABLE 7

Stick Thickness of Roller Compacted Samples

| Sample Time | 5 minutes | 10 minutes | 15 minutes | Recycled |
|---|---|---|---|---|
| average thickness (mm) | 4.32 | 3.85 | 3.95 | 3.84 |
| S.D. (mm) | 0.02 | 0.06 | 0.03 | 0.03 |
| R.S.D. (%) | 0.46 | 1.56 | 0.76 | 0.78 |

The final blend was prepared for encapsulation by milling the compacted material through an #18 mesh (1 mm) screen.

Comparison of Final Blend of "Dry" Granulated vs Final Blend of "Wet" Granulated A quantity of commercial blend for Mexitil® capsules produced by a "wet" granulation process was supplied by the manufacturer for evaluation purposes. The powders produced by the two different processes were compared to each other and to a physical mix (Formula Blend) of the ingredients. Sieve analysis, density and flow studies were evaluated.

It can be seen from the following data (Table 8) that the Formula Blend which was the starting material for both the dry and wet granulation (without lubricant) had the smallest particle size distribution with particles <63 $\mu$m accounting for greater than 75% by weight of all particles. The dry granulate had the largest or most coarse particle distribution, with the majority of particles above 125 $\mu$m. The wet granulate had the majority of its particles below 125 $\mu$m.

TABLE 8

Comparison of Process Particle Size Differences

| Particle Size (μm) | Formula Blend % Retained | Dry Granulate % Retained | Wet Granulate % Retained |
|---|---|---|---|
| 1000 | 0.81 | 1.82 | 1.11 |
| 500 | 7.09 | 36.97 | 15.14 |
| 250 | 7.99 | 25.45 | 15.54 |
| 125 | 4.86 | 11.41 | 11.41 |
| 63 | 3.54 | 5.25 | 10.19 |
| <63 | 75.53 | 18.79 | 46.62 |

The bulk and tap densities of the dry and wet granulates (Table 9) were significantly greater than for the Formula Blend. However, they were similar to each other. The flow through funnel studies showed that the Formula Blend had the slowest flow through the orifice with the dry granulate being slower than the wet granulate. It was also observed in the subsequent encapsulation work, that qualitatively, the dry granulate was less dusty and flowed visually better than the wet granulation material. The angle of repose measurements could not be correlated to any visual attributes in regard to flow for these materials. Values less than 40° are desirable to have good flow potential. [Lachmman et al., *The Theory and Practice of Industrial Pharmacy*, p. 67 (1986).].

TABLE 9

Comparison of Process Powder Characteristics

| Test | Formula Blend | Dry Granulate | Wet Granulate |
|---|---|---|---|
| Bulk Density (g/mL) | 0.23 | 0.49 | 0.47 |
| Tap Density (g/mL) | 0.43 | 0.74 | 0.71 |
| Flow Rate (g/sec.) | 4.3 | 7.3 | 9.4 |
| Angle of Repose ° | 11 | 24 | 9 |

Comparison of Processing of Final Blend of "Dry" Granulated vs Final Blend of "Wet" Granulated into Capsules Approximately 3.5 kg of complete powder blend from each granulation (dry, wet) was encapsulated with the same equipment and under the same process parameters. The batches were sampled throughout the run. Samples taken for testing included content uniformity, dissolution and weight variation. From a process stand point, each granulation processed similarly.

Capsule Weight and Content Uniformity

Time samples taken to evaluate weight uniformity are presented in Table 10. They showed that both formulas had satisfactory flow to yield uniform capsule weights.

TABLE 10

Weight Variation of Filled Capsules Between Processes

| Sample | Dry Granulate Average (mg) s.d. (mg) c.v. (%) | Wet Granulate Average (mg) s.d. (mg) c.v. (%) |
|---|---|---|
| 0 (minutes) | 400.2 7.4 1.8 | 390.6 5.7 1.5 |
| 15 (minutes) | 395.9 6.2 1.6 | 395.2 8.2 2.1 |
| 30 (minutes) | 395.3 7.7 1.9 | 391.3 9.4 2.4 |
| 45 (minutes) | 400.0 4.9 1.2 | 396.3 7.6 1.9 |
| 60 (minutes) | 397.6 7.9 2.0 | 403.9 6.6 1.6 |

Another measure of the uniformity of each formula was the capsule content uniformity. Although both processes yielded capsules with acceptable content uniformity, the dry granulated product had better capsule uniformity that the wet granulated product with about half the content variation (Table 11).

TABLE 11

Content Uniformity of Capsules Between Processes

| Capsule # | From "WET" Granulation (percent of label claim) | From "Dry" Granulation (percent of label claim) |
|---|---|---|
| 1 | 97.0 | 99.9 |
| 2 | 98.0 | 98.5 |
| 3 | 95.6 | 91.9 |
| 4 | 95.6 | 96.4 |
| 5 | 97.3 | 90.8 |
| 6 | 93.7 | 97.4 |
| 7 | 99.6 | 98.0 |
| 8 | 85.3 | 95.0 |
| 9 | 101.7 | 98.1 |
| 10 | 100.9 | 95.3 |
| 11 | 88.9 | 93.3 |
| 12 | 92.8 | 96.9 |
| 13 | 92.6 | 98.1 |
| 14 | 100.2 | 99.9 |
| 15 | 99.5 | 94.0 |
| average | 95.9 | 96.6 |
| SD | 4.6 | 2.4 |
| RSD | 4.8 | 2.5 |

Capsule Dissolution

Figure 3:
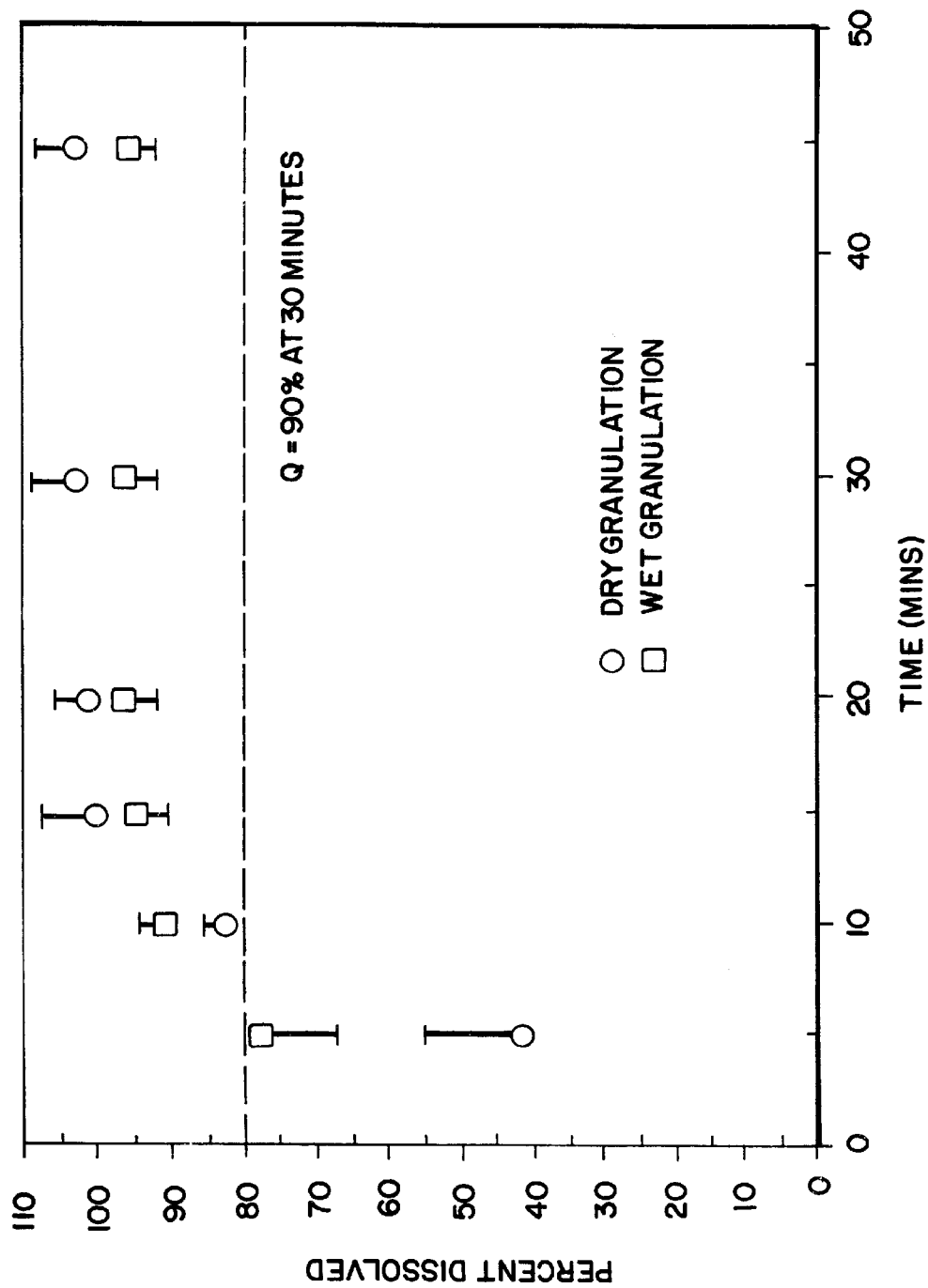
FIG. 3 is a graph comparing dissolution characteristics of a "wet" granulation with a compacted or "dry" granulation, both of mexiletine hydrochloride formulation.

Capsule dissolution (specification: Q=80% in 30 minutes) between the two processes showed that each process produced acceptable capsules which were similarly dissolving with about the same amount of variability (FIG. 3). Dissolution values (n=18) for the comparison of the wet and dry granulated products for the 15, 20, 30, and 45 minute time samples are presented in Table 12. Comparison of the dissolution profiles between the wet and dry granulated capsule products using the SUPAC Similarity Factor ($f_2$) indicated that the dissolution data for the 20, 30, and 45 minute samples are equivalent (Table 13). The 15 minute dissolution values were not considered similar with a $f_2$ value of 48.03 (values between 50 and 100 indicate in-vitro statistical equivalence of dissolution) and may reflect possible differences in initial disintegration of the filled capsules.

TABLE 12

Dissolution Data Values for "Wet" and "Dry" Granulated Products

| % Dissolved at 15 minutes | | % Dissolved at 20 minutes | | % Dissolved at 30 minutes | | % Dissolved at 45 minutes | |
|---|---|---|---|---|---|---|---|
| wet granulated | dry granulated | wet granulated | dry granulated | wet granulated | dry granulated | wet granulated | dry granulated |
| 103.23 | 105.99 | 101.37 | 103.21 | 102.73 | 102.44 | 102.57 | 100.88 |
| 88.70 | 114.10 | 91.00 | 102.72 | 97.34 | 112.49 | 97.38 | 115.30 |
| 96.14 | 113.94 | 92.25 | 113.52 | 94.28 | 115.19 | 93.50 | 104.02 |
| 92.61 | 107.01 | 93.70 | 102.15 | 96.34 | 112.70 | 95.07 | 108.47 |
| 93.65 | 99.48 | 95.80 | 102.68 | 100.74 | 99.98 | 95.63 | 103.34 |
| 85.31 | 106.46 | 92.03 | 107.00 | 94.92 | 106.93 | 97.87 | 111.80 |
| 92.68 | 100.09 | 87.28 | 99.68 | 89.18 | 100.24 | 89.20 | 101.08 |
| 100.87 | 89.65 | 102.56 | 95.66 | 101.20 | 100.16 | 99.74 | 101.83 |
| 94.75 | 102.24 | 96.02 | 99.53 | 87.03 | 99.03 | 92.04 | 99.31 |
| 95.60 | 95.89 | 86.30 | 102.76 | 97.10 | 100.31 | 88.93 | 102.83 |
| 100.62 | 94.56 | 98.73 | 96.34 | 88.57 | 95.62 | 97.29 | 102.49 |
| 94.59 | 94.40 | 97.21 | 99.89 | 95.41 | 98.59 | 94.06 | 99.03 |
| 87.27 | 100.10 | 96.30 | 99.70 | 97.27 | 101.81 | 98.23 | 100.04 |
| 94.16 | 95.05 | 99.06 | 97.50 | 94.57 | 101.00 | 97.79 | 93.64 |
| 96.66 | 100.07 | 100.64 | 103.37 | 95.92 | 101.54 | 96.96 | 100.00 |
| 95.91 | 93.55 | 100.67 | 101.47 | 99.87 | 104.46 | 92.30 | 105.99 |
| 96.60 | 96.72 | 101.72 | 99.33 | 99.85 | 101.50 | 93.73 | 101.79 |
| 93.23 | 88.14 | 101.38 | 94.09 | 96.58 | 103.49 | 93.68 | 104.47 |
| av. = 94.58 | 99.86 | 96.33 | 101.14 | 96.05 | 103.19 | 95.33 | 103.13 |
| Sd = 4.53 | 7.39 | 4.99 | 4.43 | 4.33 | 5.32 | 3.53 | 4.95 |
| RSD = 4.79 | 7.40 | 5.18 | 4.38 | 4.51 | 5.16 | 3.70 | 4.80 |

TABLE 13

Dissolution SUPAC Similarity Factor Between "Wet" and "Dry" Granulated Capsule Batches $$f_2 = 50 \log \{[1 + 1/n\Sigma^n t = 1(R_t - T_t)^2]^{-0.5} \times 100\}$$

| Sample Time | $f_2$ Value (n = 18) |
|---|---|
| 15 minutes | 48.03 |
| 20 minute | 51.75 |
| 30 minute | 51.28 |
| 45 minute | 50.45 |

Note:
Value ≧50 are considered to have equivalent dissolution performance.

CONCLUSION

Feasibility testing of Mexitil® active ingredient (mexiletine) and formula blend indicated that both the drug substance and the formula blend could be dry granulated.

While the invention has been described with reference to specific materials and techniques, it is understood that such invention is not limited to such materials and techniques. Variations in such materials and techniques would be apparent to an individual skilled in the art. Accordingly, the present invention is defined and limited as set forth in the appended claims.

What is claimed is:

1. In a method for densification of mexiletine hydrochloride crystals for use in a powder to be placed in capsules for oral administration, the improvement which comprises subjecting the mexiletine hydrochloride crystals together with one or more pharmaceutical excipients to a pressure of between about 6,600 psi to about 50,000 psi.

2. The improvement as recited in claim 1 wherein the pressure is between about 6,600 psi to about 25,000 psi.

* * * * *